US011305098B2

(12) United States Patent
Zhou et al.

(10) Patent No.: US 11,305,098 B2
(45) Date of Patent: *Apr. 19, 2022

(54) METHODS OF FABRICATING AN INFLATABLE BALLOON

(71) Applicant: Edwards Lifesciences Corporation, Irvine, CA (US)

(72) Inventors: Pu Zhou, Dove Canyon, CA (US); Bin Tian, Irvine, CA (US); Yidong M. Zhu, Irvine, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/940,833

(22) Filed: Jul. 28, 2020

(65) Prior Publication Data

US 2020/0353227 A1 Nov. 12, 2020

Related U.S. Application Data

(60) Continuation of application No. 15/815,599, filed on Nov. 16, 2017, now Pat. No. 10,722,693, which is a
(Continued)

(51) Int. Cl.
*B23K 26/0622* (2014.01)
*A61M 25/10* (2013.01)
(Continued)

(52) U.S. Cl.
CPC ......... *A61M 25/1029* (2013.01); *B21D 39/00* (2013.01); *B23K 26/0624* (2015.10);
(Continued)

(58) Field of Classification Search
CPC ...... A61M 25/1029; A61M 2025/1031; A61M 2025/1086; A61M 2025/107;
(Continued)

(56) References Cited

U.S. PATENT DOCUMENTS

| 4,035,849 A | 7/1977 | Angell et al. |
| 4,592,340 A | 6/1986 | Boyles |

(Continued)

FOREIGN PATENT DOCUMENTS

| DE | 19532846 A1 | 3/1997 |
| DE | 19907646 A1 | 8/2000 |

(Continued)

*Primary Examiner* — Jermie E Cozart
(74) *Attorney, Agent, or Firm* — Guy L. Cumberbatch; Joel B. German

(57) ABSTRACT

Inflatable devices are disclosed including a surface which has a network of polymer chains and is configured to be inflatable into a therapeutically or diagnostically useful shape, and at least one ultrashort laser pulse-formed modification in the surface. The network can, for example, include a network morphology that is substantially unchanged by modification with the ultrashort pulse laser. Ultrashort laser pulses can be laser pulses equal to or less than 1000 picoseconds in duration. Advantageously, the etching process uses a relatively low-heat laser to avoid significant heating of surrounding polymers while modifying the surface (and other structures) of the device. The process is configured so that the polymer chain morphology adjacent the modification is substantially unaffected by the low-heat laser. The resulting inflatable device has customized surface features while still retaining substantially homogenous polymer network morphology. This preserves the elasticity, especially the surface elasticity, of the inflatable device.

20 Claims, 11 Drawing Sheets

Related U.S. Application Data division of application No. 14/938,761, filed on Nov. 11, 2015, now abandoned.

(60) Provisional application No. 62/082,241, filed on Nov. 20, 2014.

(51) Int. Cl.

| | |
|---|---|
| *B23K 26/362* | (2014.01) |
| *B23K 26/402* | (2014.01) |
| *B23K 26/361* | (2014.01) |
| *B21D 39/00* | (2006.01) |
| *B23K 26/06* | (2014.01) |
| *B23K 103/00* | (2006.01) |

(52) U.S. Cl.
CPC ........ *B23K 26/0626* (2013.01); *B23K 26/361* (2015.10); *B23K 26/362* (2013.01); *B23K 26/402* (2013.01); *A61M 2025/107* (2013.01); *A61M 2025/1031* (2013.01); *A61M 2025/1075* (2013.01); *A61M 2025/1079* (2013.01); *A61M 2025/1084* (2013.01); *A61M 2025/1086* (2013.01); *A61M 2025/1088* (2013.01); *B23K 2103/42* (2018.08); *B23K 2103/50* (2018.08)

(58) Field of Classification Search
CPC .. A61M 2025/1075; A61M 2025/1079; A61M 2025/1084; A61M 2025/1088; A61M 2025/1034; B23K 26/0624; B23K 26/0626; B23K 26/361; B23K 26/362; B23K 2103/50; B21D 39/00
See application file for complete search history.

(56) References Cited

U.S. PATENT DOCUMENTS

| | | | |
|---|---|---|---|
| 4,796,629 A | 1/1989 | Grayzel | |
| 4,878,495 A | 11/1989 | Grayzel | |
| 4,986,830 A | 1/1991 | Owens et al. | |
| 4,994,077 A | 2/1991 | Dobben | |
| 5,059,177 A | 10/1991 | Towne et al. | |
| 5,411,552 A | 5/1995 | Andersen et al. | |
| 5,545,209 A | 8/1996 | Roberts et al. | |
| 5,554,185 A | 9/1996 | Block et al. | |
| 5,591,195 A | 1/1997 | Taheri et al. | |
| 5,599,305 A | 2/1997 | Hermann et al. | |
| 5,639,274 A | 6/1997 | Fischell et al. | |
| 5,728,068 A | 3/1998 | Leone et al. | |
| 5,733,301 A * | 3/1998 | Forman ............ | A61M 25/1029 604/96.01 |
| 5,826,588 A | 10/1998 | Forman | |
| 5,840,081 A | 11/1998 | Andersen et al. | |
| 5,968,068 A | 10/1999 | Dehdashtian et al. | |
| 6,168,614 B1 | 1/2001 | Andersen et al. | |
| 6,174,327 B1 | 1/2001 | Mertens et al. | |
| 6,217,585 B1 | 4/2001 | Houser et al. | |
| 6,379,372 B1 | 4/2002 | Dehdashtian et al. | |
| 6,454,799 B1 | 9/2002 | Schreck | |
| 6,458,153 B1 | 10/2002 | Bailey et al. | |
| 6,461,382 B1 | 10/2002 | Cao | |
| 6,527,979 B2 | 3/2003 | Constantz | |
| 6,582,462 B1 | 6/2003 | Andersen et al. | |
| 6,652,568 B1 * | 11/2003 | Becker ................ | A61F 2/958 604/103.1 |
| 6,652,578 B2 | 11/2003 | Bailey et al. | |
| 6,730,118 B2 | 5/2004 | Spenser et al. | |
| 6,733,525 B2 | 5/2004 | Yang et al. | |
| 6,767,362 B2 | 7/2004 | Schreck | |
| 6,830,584 B1 | 12/2004 | Seguin | |
| 6,893,460 B2 | 5/2005 | Spenser et al. | |
| 6,908,481 B2 | 6/2005 | Cribier | |
| 7,018,406 B2 | 3/2006 | Seguin et al. | |
| 7,018,408 B2 | 3/2006 | Bailey et al. | |
| 7,276,084 B2 | 10/2007 | Yang et al. | |
| 7,318,278 B2 | 1/2008 | Zhang et al. | |
| 7,374,571 B2 | 5/2008 | Pease et al. | |
| 7,393,360 B2 | 7/2008 | Spenser et al. | |
| 7,462,191 B2 | 12/2008 | Spenser et al. | |
| 7,510,575 B2 | 3/2009 | Spenser et al. | |
| 7,585,321 B2 | 9/2009 | Cribier | |
| 7,618,446 B2 | 11/2009 | Andersen et al. | |
| 7,785,366 B2 | 8/2010 | Maurer et al. | |
| 8,029,556 B2 | 10/2011 | Rowe | |
| 8,167,932 B2 | 5/2012 | Bourang | |
| 8,449,606 B2 | 5/2013 | Eliasen et al. | |
| 10,722,693 B2 * | 7/2020 | Zhou ................ | B23K 26/0626 |
| 2002/0032481 A1 | 3/2002 | Gabbay | |
| 2003/0050694 A1 | 3/2003 | Yang et al. | |
| 2003/0158597 A1 | 8/2003 | Quiachon et al. | |
| 2004/0133263 A1 | 7/2004 | Dusbabek et al. | |
| 2004/0186565 A1 | 9/2004 | Schreck | |
| 2004/0260389 A1 | 12/2004 | Case et al. | |
| 2005/0070996 A1 | 3/2005 | Dinh et al. | |
| 2005/0096736 A1 | 5/2005 | Osse et al. | |
| 2005/0203614 A1 | 9/2005 | Forster et al. | |
| 2005/0203617 A1 | 9/2005 | Forster et al. | |
| 2006/0025857 A1 | 2/2006 | Bergheim et al. | |
| 2007/0005131 A1 | 1/2007 | Taylor | |
| 2007/0203575 A1 | 8/2007 | Forster et al. | |
| 2007/0265700 A1 | 11/2007 | Eliasen et al. | |
| 2008/0065011 A1 | 3/2008 | Marchand et al. | |
| 2008/0125853 A1 | 5/2008 | Bailey et al. | |
| 2008/0294230 A1 | 11/2008 | Parker | |
| 2009/0157175 A1 | 6/2009 | Benichou | |
| 2009/0276040 A1 | 11/2009 | Rowe et al. | |
| 2009/0281619 A1 | 11/2009 | Le et al. | |
| 2009/0319037 A1 | 12/2009 | Rowe et al. | |
| 2010/0049313 A1 | 2/2010 | Alon et al. | |
| 2010/0198347 A1 | 8/2010 | Zakay et al. | |
| 2011/0015729 A1 | 1/2011 | Jimenez et al. | |
| 2011/0284498 A1 | 11/2011 | Warnack et al. | |
| 2012/0073733 A1 | 3/2012 | Ngo et al. | |
| 2012/0123529 A1 | 5/2012 | Levi et al. | |
| 2013/0197353 A1 | 8/2013 | Von Oepen | |
| 2013/0317598 A1 | 11/2013 | Rowe et al. | |

FOREIGN PATENT DOCUMENTS

| | | |
|---|---|---|
| EP | 0592410 B1 | 10/1995 |
| EP | 0850607 A1 | 7/1998 |
| EP | 1796597 A2 | 6/2007 |
| FR | 2815844 A1 | 5/2002 |
| WO | 9117720 A1 | 11/1991 |
| WO | 9829057 A1 | 7/1998 |
| WO | 9940964 A1 | 8/1999 |
| WO | 0149213 A2 | 7/2001 |
| WO | 0154625 A1 | 8/2001 |
| WO | 0176510 A2 | 10/2001 |
| WO | 0222054 A1 | 3/2002 |
| WO | 0236048 A1 | 5/2002 |
| WO | 0247575 A2 | 6/2002 |
| WO | 03047468 A1 | 6/2003 |
| WO | 2005084595 A1 | 9/2005 |
| WO | 2006111391 A1 | 10/2006 |
| WO | 2006138173 A2 | 12/2006 |
| WO | 2005102015 A3 | 4/2007 |
| WO | 2007047488 A2 | 4/2007 |
| WO | 2007067942 A1 | 6/2007 |
| WO | 2010121076 A2 | 10/2010 |
| WO | 2012-156914 A2 | 11/2012 |

\* cited by examiner

METHODS OF FABRICATING AN INFLATABLE BALLOON

RELATED APPLICATIONS

The present application is a continuation of U.S. application Ser. No. 15/815,599, filed Nov. 16, 2017, which is a divisional of U.S. application Ser. No. 14/938,761, filed Nov. 11, 2015, which claims the benefit of priority to U.S. Provisional Application No. 62/082,241, filed Nov. 20, 2014, which is incorporated by reference in its entirety for all purposes.

FIELD OF THE INVENTION

This invention relates to the field of inflatable medical devices for diagnostic and therapeutic applications, particularly those designed to expand within an anatomical space.

BACKGROUND OF THE INVENTION

Inflatable devices are used in many surgical and minimally invasive surgical (MIS) techniques and settings. Medical balloons with thinner walls, higher strength, and smaller profiles are designed to withstand high inflation pressures and are well suited for use in a broad range of diagnostic and therapeutic procedures. They can be produced in a variety of lengths, diameters, and shapes, including complex custom shapes for specific applications, and supplied with specialty coatings for added performance. In a typical MIS procedure, uninflated devices are positioned within an anatomical space and then filled with air or fluid to expand the device and possibly the anatomical space itself. This procedure is used to deliver a prosthetic heart valve or stent to a cardiac or vascular structure. Alternatively, an inflatable device can be used to dilate an anatomical structure, as in angioplasty procedures. Other surgical procedures that incorporate the use of inflatable devices include, for example, kyphoplasty, nephrostomy, gastric balloon placement, endometrial ablation, laparoscopic hernia repair and renal denervation. Furthermore, inflatable devices can be used in the obstruction, dilation and/or stent placement within the following anatomical structures: sinuses, intestines, lacrimal ducts, Carpal tunnels, Eustachian tubes, the uterus, ureters, bile ducts, the trachea, the esophagus, the urethra, and the nasal passages. This list does not include all procedures that use inflatable devices, but is meant to demonstrate the breadth of this invention's relevance.

By way of example, inflatable devices are used in transcatheter aortic heart valve delivery procedures. In this procedure, a guidewire is delivered through the femoral artery, through the patient's vasculature to the native aortic valve, and placed within the left ventricle. A first balloon mounted on a catheter is inserted over the guidewire into the aortic valve and inflated to widen the structure. The first balloon is removed back down the guidewire. A second, folded balloon carrying the new prosthetic heart valve is delivered to the patient's diseased aortic valve. Alternatively, a prosthetic heart valve may be moved onto the balloon once it is inside the patient's body. Once positioned, the folded balloon is inflated and the previously crimped valve is expanded to its full diameter. At its full diameter, the stent is lodged within the native heart valve. The second balloon is deflated and is routed back down the patient's vasculature and out the femoral artery via the guidewire, leaving the new valve in place.

Given their role in treating a range of patient conditions, improvements in inflatable devices are highly desirable.

SUMMARY OF THE INVENTION

The inventors have advantageously modified the surface (and other structures) of inflatable devices, such as balloons, using low heat lasers, such as ultrashort pulse lasers, while avoiding significant heating of the polymer surrounding the modification. The inventors have configured the process so that the polymer chain network morphology surrounding the modification is substantially unaffected by thermal effects. The resulting inflatable device has customized surface features while still retaining a substantially unchanged polymer network morphology surrounding the low heat laser-formed modification. This preserves the elasticity and other mechanical properties of the inflatable device.

In one implementation, ultrashort laser pulses can be laser pulses equal to or less than 1000 picoseconds in duration. In another implementation, ultrashort laser pulses can be equal to or less than 1000 femtoseconds in duration.

In one implementation, the inflatable devices have a wall which has a surface. The wall is configured to be inflatable into a therapeutically useful shape. The wall also has at least one low heat (or ultrashort) laser-formed modification on the surface. The wall is at least partially formed of a polymer, and therefore has a network of polymer chains. The network of polymer chains can have a network morphology. The network morphology surrounding the low heat laser-formed modification is substantially unaffected by thermal effects.

The therapeutically useful shape can include a body, leg and cone regions. These regions are arranged along a longitudinal axis that extends through them.

The laser formed modification can be on the inner surface of the wall of the device. For example, the low heat laser formed modification can be on an inner surface of the leg region.

In other implementations, the device can have multiple layers, such as an inner layer and an outer layer. The low heat laser-formed modification can include a recession formed on the outer layer. The outer layer can be radiopaque to facilitate locating it during surgical procedures.

The low heat laser-formed modification, for example, can be one or more recessions in the surface. The recessions can, for example, increase friction on the surface of the inflatable device. The recessions can have different configurations. For example, the recessions can extend parallel to the longitudinal axis of the device. The recessions can be in a spaced, parallel arrangement and extend circumferentially around the body region.

The device can include a circumferential perimeter. The recession in the surface extends around at least a portion of the circumferential perimeter. The recession can even extend entirely or fully around the circumferential perimeter. The inflatable device can include a plurality of the circumferentially extending recessions. They can be spaced apart from each other and in a parallel arrangement, forming a stripe-like pattern.

In another implementation, the recession can be etched into the cone region of the device. For example, the recession can extend from adjacent the leg region to the body region. And, the recession can continue over an axial length of the body region. In an implementation with two cone regions, the recession can extend over both cone regions as well as the body region.

The inflatable device can include a plurality of recessions. The recessions can be on the cone region and extend only partially between the leg and body regions. The recessions themselves can change in width, such as by tapering as they extend toward the leg region.

The plurality of recessions can have geometric shapes, such as circles. For example, the circles can be etched in a pattern on the body region of the device.

Methods include fabricating an inflatable device by applying low heat laser pulses to a surface of the inflatable device. And, the low heat laser pulses can be applied to leave a network morphology surrounding the modification substantially unaffected by thermal effects.

The method can also include forming a body, leg and cone regions about a longitudinal axis extends through the regions. The low heat laser pulses can be applied to increase or reduce a friction of the surface.

The low heat laser pulses could be applied to an inner or outer surface of the inflatable device. For example, the inner surface could be partially ablated to remove material.

In a multi-layered wall, the low heat laser pulses can be used to reveal an inner layer beneath an outer layer. In this manner, excess material of the outer layer serving no functional benefit can be removed.

The different regions can also be ablated, such as the cone, body and leg regions, selectively, for desired performance parameters. For example, the method can include ablating circumferentially around the body of the inflatable device to form strips or stripes.

The application of low heat laser pulses can include applying ultrashort laser pulses equal to or less than 1000 picoseconds in duration. In another implementation, ultrashort laser pulses can be equal to or less than 1000 femtoseconds in duration.

Ultrashort laser pulse-formed modifications can enable tighter folding, more predictable burst pressure, better bonding to external devices such as catheters, the ability to coordinate inflation of various parts of the device, addition of friction or physical features that prevent sliding of above-lying surfaces (such as valves or stents), removal of additional surface layers from selected areas of the device, and/or addition of markings that would assist during folding or during surgical procedures.

These and other features and advantages of the implementations of the present disclosure will become more readily apparent to those skilled in the art upon consideration of the following detailed description and accompanying drawings, which describe both the preferred and alternative implementations of the present disclosure.

DESCRIPTION OF THE PREFERRED EMBODIMENTS

Figure 1A:
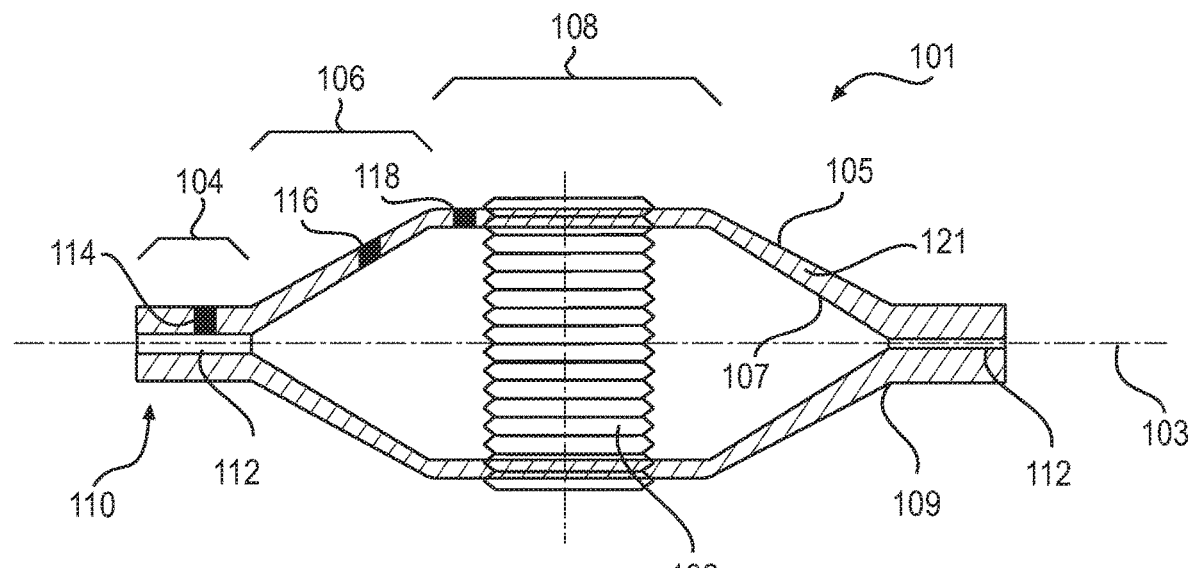
FIGS. 1A-1C are schematics of inflatable devices prior to the low heat laser pulse-formed modifications.

Disclosed herein are embodiments of inflatable devices with special surface features created or facilitated by low heat, or ultrashort, laser pulse formed modifications. Implementations of the present disclosure now will be described more fully. Indeed, these implementations can be embodied in many different forms and should not be construed as limited to the implementations set forth herein; rather, these implementations are provided so that this disclosure will satisfy applicable legal requirements. The following description of certain examples of an inflatable device should not be used to limit the scope. Other examples, features, aspects, embodiments, and advantages of the inflatable medical device will become apparent to those skilled in the art from the following description. As will be realized, the inflatable device is capable of additional aspects, all without departing from the spirit of the inflatable device. Accordingly, the drawings and descriptions should be regarded as illustrative in nature and not restrictive.

For purposes of this description, certain aspects, advantages, and novel features of the embodiments of this disclosure are described herein. The described methods, systems, and apparatus should not be construed as limiting in any way. Instead, the present disclosure is directed toward all novel and nonobvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved.

Features, integers, characteristics, compounds, chemical moieties, or groups described in conjunction with a particular aspect, embodiment or example of the invention are to be understood to be applicable to any other aspect, embodiment or example described herein unless incompatible therewith. All of the features disclosed in this specification (including any accompanying claims, abstract, and drawings), and/or all of the steps of any method or process so disclosed, can be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract, and drawings), or to any novel one, or any novel combination, of the steps of any method or process so disclosed It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

As used in the specification, and in the appended claims, the singular forms "a", "an", "the", include plural referents unless the context clearly dictates otherwise. The term "comprising" and variations thereof as used herein is used synonymously with the term "including" and variations thereof and are open, non-limiting terms.

As used herein, inflatable devices include medical balloons. For example, inflatable devices include medical balloons such as those used in therapeutic or diagnostic procedures.

As used herein, ablating or etching is a process by which material is removed using a laser. Modifications to an inflatable device, for example, low heat-laser pulse formed modifications, can be formed by ablating or etching.

The inventors have noted several shortcomings in inflatable devices of the prior art. They have endeavored to address these shortcomings by implementing the principles of this invention. Inflatable device surface modifications are desirable for many reasons, which will be explained in greater detail below. However, modification with laser pulses can overheat the polymer, disorienting the network of polymer chains that surround the modification. This disorientation decreases the overall strength of the device.

The inventors have designed a process wherein modifications by a relatively low heat laser (e.g., ultrashort pulse laser) do not heat the surrounding polymer. Additional details of such low heat lasers or ultrashort pulse lasers are disclosed in U.S. Patent Application Publication No. 2013/0110097 filed Sep. 17, 2012, which is incorporated herein by reference. The polymer chain network morphology in the area surrounding the laser pulse-formed modification is substantially unaffected by thermal effects, preserving the strength of the device. Low heat or ultrashort laser pulses as used herein are defined as laser pulses less than 1000 picoseconds in duration. In some implementations, low heat or ultrashort laser pulses can be less than 1000 femtoseconds in duration.

The inventors have realized or determined several design considerations during their development of the implementations of the invention. Procedures using inflatable devices benefit from transfer through narrow anatomical spaces in an uninflated state. To achieve this, the inflatable devices can benefit from being tightly folded underneath an external device such as a valve or stent. The device in its folded state should generally have a narrow profile. This enables it to enter smaller anatomical spaces, reducing tissue damage. It also enables easier delivery with lower friction.

However, certain fabrication processes create unnecessary bulk. For example, one method of producing an inflatable device is to blow mold a polymer tube into a balloon shape. This forms thinner areas that will ultimately inflate to wider dimensions, creating the body of the device. The areas outside the mold are not meant to inflate. These become the legs of the device. The transition from the thinner body area to the thicker leg region is the cone of the device. In this region, the wall changes from thin to thick. If the walls of these regions could be thinned, the overall profile of the folded inflatable device would be thinner and could fit into narrower anatomical spaces. Low heat laser pulse formed modifications can be used to even the wall thickness post-molding, improving the consistency of the bonding strength of the inflatable devices to external devices such as catheters. Furthermore, the low heat lasers could be used to newly create features that enhance bonding to external devices.

Precisely targeted placement and orientation of a valve or stent along an inflatable device is a factor in the success of the procedure and to the safety of the patient. Proper timing of inflation is important to reduce flaring of the ends of the valve or stent. Similarly, a valve or stent increases the resistance to inflation, and areas of the inflatable device around the external device can inflate first. This creates an undesirable dog-bone shape. Improvements to valve stabilization and inflation timing would be highly beneficial, as would the improvements in the visualization of the inflatable device during delivery for assisting in orientation of the valve/stent.

The inventors have further observed that inflatable devices could benefit from heightened predictability of bursting pressure. The ability to create inflatable devices with consistent wall thicknesses would enhance the prediction of burst pressure. Furthermore, the ability to thin a specific region of an inflatable device would enable prediction of the precise bursting location, and to locate it to the region that would cause the least tissue damage, should it ever occur. Precise manufacturing can even allow for the design of inflatable devices that leak slowly and gently instead of bursting.

The inventors have addressed these issues by removing material from precise locations of the inflatable device using a low heat laser. Methods of laser-ablating excess material after molding have been disclosed in the prior art, such as in U.S. Pat. No. 6,719,774. However, the utility of such methods is limited because heat produced by the laser causes disorientation of the nearby polymer network, which increases chances of bursting at lower inflation pressures. In contrast, alignment of the network of polymer chains is associated with increased resistance to bursting. Thus, the maintenance of an oriented morphology is desirable for inflatable devices.

The inventors have determined that ultrashort laser pulses have a non-thermal laser-material coupling that protects against deleterious effects to the polymer network adjacent to the laser modification. The term "low heat laser" as defined herein includes lasers that can be operated to ablate the polymeric wall compositions at temperatures less than a temperature at which the adjacent polymeric wall composition and/or organization starts to degrade. Generally, most bio-absorbable and many bio-compatible polymers have a melting point of below 100 degrees Celsius. The low heat lasers can be, for example, near-IR laser systems that have a maximum pulse energy of 40 micro-joules with a pulse duration of less than 400 femtoseconds at 200 KHz. Another example system has a maximum pulse energy of 200 micro-joules with a pulse duration of 10 picoseconds. Still another example system is a fiber-based ultrafast laser that is mode-locked and can generate ultrashort pulses centered at about 1552.2 nanometers. The power of this system can be 5, 10 or 20 watts. The pulses produced can be less than 800 femtoseconds.

FIGS. 1A-D show examples of inflatable devices prior to modification by low heat lasers. These exemplary devices are manufactured by molding a polymer tube into a balloon shape. This fabrication process creates certain characteristics that are improved by the modifications disclosed herein.

Inflatable devices can be fabricated to suit various anatomical structures without detracting from the function of the device.

An inflatable device 101 that has not yet been modified by ultrashort laser pulses is shown in FIGS. 1A-D. As used herein, the terms "modify", "modified", and "modifications" refer to actions of the ultrashort laser pulses on the inflatable device surface. The term "unmodified" refers to prefabricated inflatable devices which have not been modified by ultrashort laser pulses. The inflatable device 101 of FIG. 1A comprises a body region 108, a pair of leg regions 104, and a pair of cone regions 106. These regions define a longitudinal axis 103 extending generally along a direction of a guide wire (not shown) supporting the device. Each of the cone regions 106 has an end 109 adjacent the leg region 104. The inflatable device further comprises a wall 121 having an outer surface 105 and an inner surface 107. The regions 104, 106 and 108 are sub-portions of the wall 121.

Implementations of the inflatable devices 101 disclosed herein can be used alone or in conjunction with other devices, including but not limited to prosthetic heart valves and stents. In this manner, a prosthetic valve 102 or other device can be delivered along with the inflatable device 101 (both in a relatively compressed configuration) to a relatively inaccessible location in the body, such as percutaneously to a non-functional native heart valve. Then the device 101 is inflated to expand the valve 102 into an expanded condition. For example, in FIG. 1A, the expanded valve 102 is situated around the expanded body region 108 of the inflatable device 101.

Referring again to FIG. 1A, the body region 108 is positioned adjacent to and extends between the cone regions 106. The body region 108 has an elongate shape (as shown by the longitudinal cross-section shown in FIG. 1A) that extends in the direction of the longitudinal axis 103. The body region 108 of the inflatable device 101 also has a transverse cross section (not shown) extending perpendicular to the longitudinal axis 103. The transverse cross section can have an extruded, symmetrical shape, such as a circular or square shape, or some other geometric or irregular shape depending upon the desired application Generally, the length and diameter of the body region 108 and the rest of the device can be adapted to suit various anatomical structures or to perform various functions. For example, FIG. 1B shows a variation on the dimensions of the body region 108. The length of body region 108 of the implementation of FIG. 1B, for example, is shorter than that of the implementation shown in FIG. 1A. The diameter of the body region 108, on the other hand, is larger in FIG. 1B than in FIG. 1A. The dimensions of the inflatable devices can also vary when they are in their crimped, folded states.

Figure 1B:
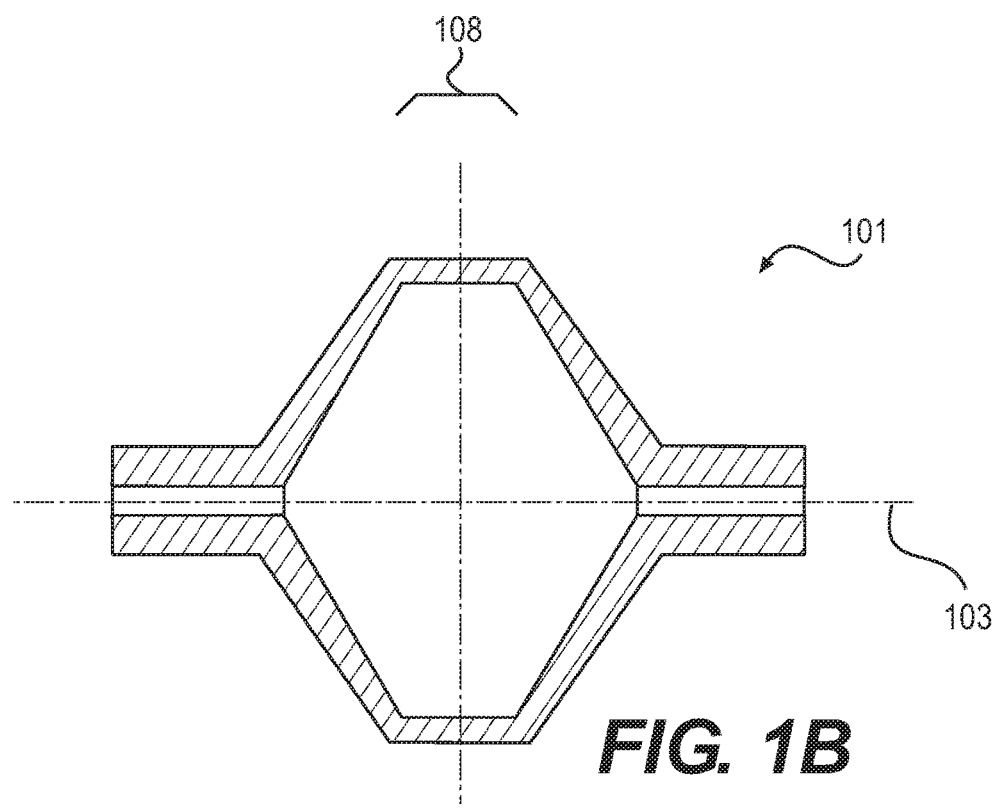

Prior to modification with ultrashort laser pulses, the body region 108 of the inflatable device 101 shown in FIG. 1A can have slight variations in wall thickness 118. These slight variations are caused by the fabrication process. In some examples, the thickness of the wall may change gradually along the length of the body region 108.

Referring again to FIGS. 1A-D, the unmodified inflatable device 101 also includes the cone regions 106. Each of the cone regions 106 extends from a wide end adjacent the body region 108 to a narrow end 109 adjacent the leg region 104. The cone regions 106 have a frustoconical shape arranged circumferentially around the longitudinal axis 103. A diameter of the cone region 106 extends perpendicular to the longitudinal axis 103.

As described above for the body region, the dimensions of the cone regions 106 vary depending upon the application.

The cone regions 106 of the inflatable device 101 shown in FIG. 1A have a cone region wall thickness 116 that tapers moving away from the narrow end 109. This variation occurs during the blow molding process, as the central region of the polymeric tube (which becomes the body region 108) is stretched to a greater extent than the edges of the tube. For example, the cone region wall thickness 116 of the unmodified inflatable device 101 can be thicker at the narrow end 109, adjacent to the leg region, than at end 108, adjacent to the body region. Similar to the body region, the fabrication process can also cause slight, localized variability in the cone region wall thickness 116.

As shown in FIG. 1A, the inflatable device 101 includes the pair of leg regions 104 at opposite ends of the inflatable device. In this implementation, the leg regions are non-inflatable ends of the wall material 121 used to construct the inflatable device. The leg regions can be compressed onto a guide wire for delivery into an anatomical space. The inflatable device is mounted onto a guide wire or catheter (not shown) via axial openings 112.

While the implementations discussed herein include a pair of leg regions, it is possible to fabricate inflatable devices with a single leg and cone region. Other implementations can have a range of shapes formed by the wall 121, such as square, bulbous or irregular shapes that do not necessarily include the particular regions 104, 106 and 108 of the illustrated implementations. These alternate implementations still benefit from the formation of modifications thereon.

The leg regions 104 extend from a cone region end 109 away from the body region 108 to a free end 110. The leg regions 104 have a length in the direction of the longitudinal axis 103 and a transverse cross section extending perpendicular to the longitudinal axis 103. The diameter and wall thickness, generally, can be a reflection of the original polymeric tube used to form the inflatable device 101. The fabrication process can cause slight variability in the leg region wall thickness 114 along its length.

The inflatable device 101 shown in FIG. 1A has a wall 121 with an outer surface 105 and an inner surface 107. The outer surface 105 is farther from the longitudinal axis 103 than the inner surface 107. The outer surface generally contacts above-lying surfaces of an external device mounted thereon, including for example the inner surfaces of a prosthetic heart valve 102 or stent.

Part of the function of the body region 108 of the inflatable device 101 is to allow axial positioning of the device or structure which it is expanding. To this end, the interface between the surface and the external device generates an improved frictional retaining force via the modifications of the surface. Another way to understand the effect of friction is to quantify the surface roughness of the inflatable device 101.

Generally the inflatable device's surfaces 105, 107, and walls 121 are formed of a polymer material, at least in part. The polymer material inherently includes a network of polymer chains having a network morphology. It is understood that the walls' 121 elasticity and other mechanical properties are affected by the network morphology of the polymer chains making up the surfaces 105, 107, walls 121, or portions thereof. Without being wed to theory, it is also understood that the network morphology is affected by the polymer chain orientation.

Although a range of materials (and combinations of materials) are capable of being inflated at the pressures needed to perform functions, polymeric materials for layers or compounds are particularly well suited for applications.

They have the flexibility to shrink to small diameters and the elasticity to expand without bursting. Polymeric materials include, for example, thermoplastic and thermoset polymers. Such polymers include, for example, PET, Nylon, Pebax, polyurethane, polyetherurathane, PVP, PEO, HDPE, and LDPE.

To fabricate an inflatable device 101, a polymer can be blow molded into a hollow balloon shape. The central region of the hollow polymer has a thinner body region 108 that will ultimately inflate to wider dimensions. The cone region 106 and its tapered wall 116 are products of this molding process. The leg regions 104 are not molded and therefore do not substantially inflate. The leg regions 104 can be bound to a catheter tube by mounting the device around openings 112 and bonding the leg material to the catheter tube. This bond can have a bonding strength that varies with size and application. The bonding strength can be measured by a tensile test. In these examples, the low heat laser modifications take place after the molding process. However, low heat laser modifications can also take place prior to the molding process without deviating from the inventive concept.

Figure 1C:
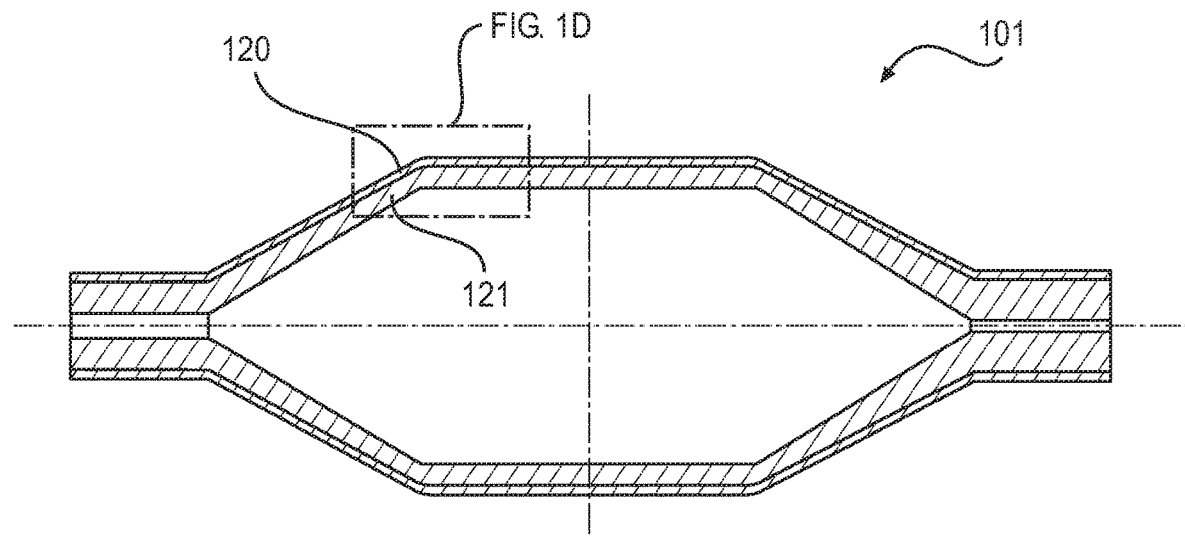
Figure 1D:
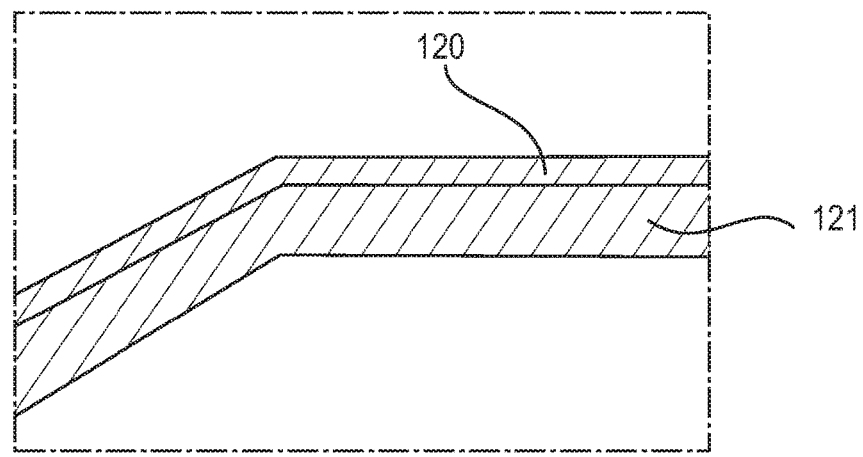
FIG. 1D is an enlarged view of the multiple layers of the inflatable device of FIG. 1C, prior to the low heat laser pulse-formed modifications.

As seen in FIG. 1C, in another implementation, inflatable device 101 has multiple wall layers 120, 121 prior to modification by ultrashort laser pulses. The outer layer 120 is the farthest layer from the longitudinal axis 103, and the inner layer 121 is closest to the longitudinal axis 103. An enlarged version of the multiple surface layer inflatable device 101 is shown in FIG. 1D.

Additional surface layers can have several functions. For example, an additional surface layer can be designed to increase friction, reduce friction, or add radiopacity to the device. And, as described below, the presence of multiple layers allows them to be selectively etched away and/or revealed to generate unique, customized properties for the inflatable devices 101.

The surface roughness of the inflatable device 101 can impact function. The outer layer 120 can be included to alter the surface roughness—such as by using a material that is inherently rougher than the inner layer 121. And, in areas where reduced roughness is desired (such as on the cone regions 106 for easier insertion into body lumens) the outer layer 120 can be etched away.

Multi-layer implementations similarly are not limited to the two layers shown in FIG. 1C. Instead, three, four or more layers can be used to customize the properties of the inflatable device 101 to different applications and for different etching effects. The layers can be fabricated from materials such as Nylon, Pebax, PET, polyurethane, polyetherurathane, PVP, PEO, HDPE, LDPE. Radiopacity can be incorporated in an outer layer by mixing the polymer solution with a pacifier, such as Tungsten powder, prior to fabrication. Platinum, gold, palladium, iridium, magnesium, zinc, tungsten, tantalum, iron, iodine salts, bismuth salts, or barium salts can also be incorporated into an outer layer to yield a radiopaque inflatable device.

Figure 2A:
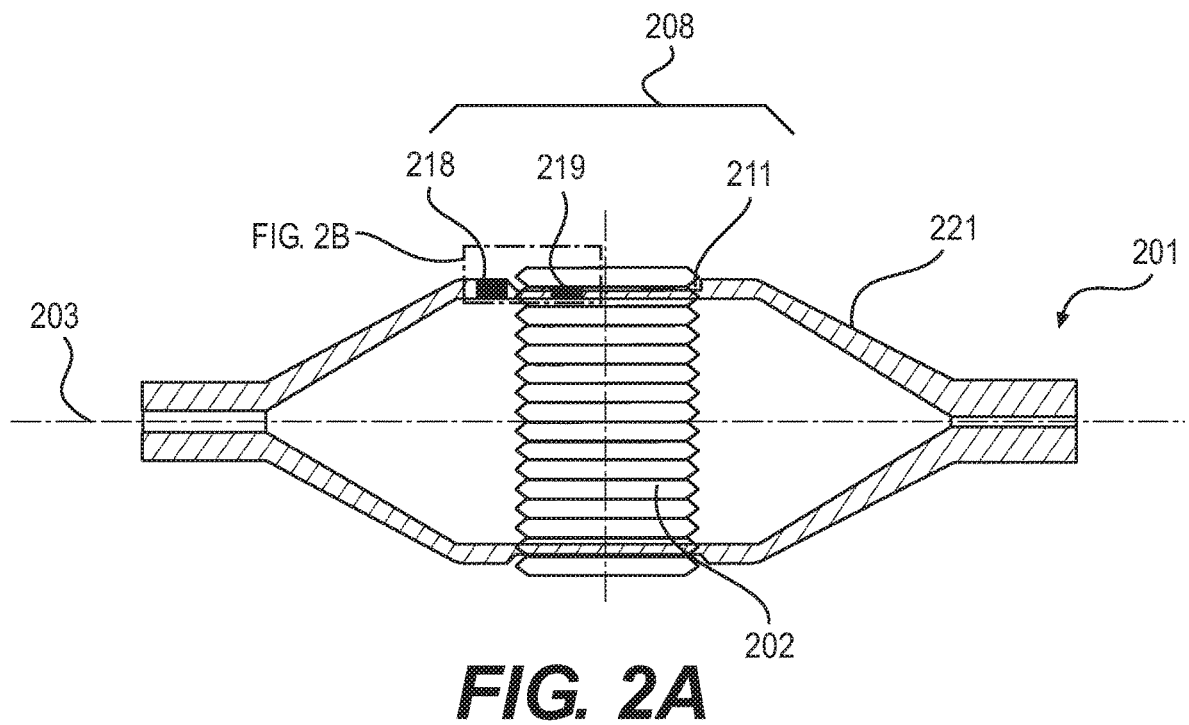
FIG. 2A is a schematic of an inflatable device after modification with low heat laser pulses.

FIG. 2A shows the inflatable device 201 of FIG. 1A with recessions formed by ultrashort laser pulses or some other low heat laser. In particular, in this implementation, the outer surface 105 of the body region 208 has been partially ablated by ultrashort laser pulses. The ablations create one or more recessions 211 in the outer surface. The recession 211 has a length that extends parallel to the longitudinal axis 203. The recession 211 also extends around a perimeter of the body 208 of the inflatable device 201—largely forming a tubular-shape of negative space in the wall 221. The length of the recession 211 in the axial direction can adapted to specific functions or applications. For example, the length can be mostly coextensive with the stent or valve 202. In this manner additional clearance is provided for crimping the valve 202 down to a smaller diameter for easier delivery.

Figure 2B:
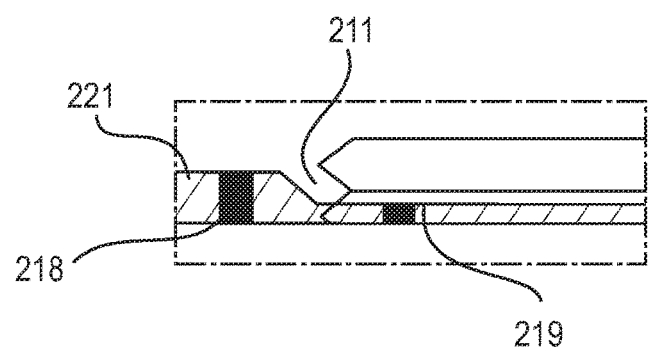
FIG. 2B is an enlarged view of a region of interest from FIG. 2A.

FIG. 2B shows an enlarged portion of FIG. 2A with the ultrashort laser pulse-formed recession 211 in the body region 208. The wall 221 of the body region has an original thickness 218 and an ablated wall thickness 219. The original thickness 218 corresponds to thickness 118 of the unmodified inflatable device 101 shown in FIG. 1A. The ablated wall thickness 219 can vary by particular desired application, but in the case of an inflatable device for expansion of a stent mounted heart valve it can be about 1-40% of the original wall thickness 218.

The recession 211 shown in FIGS. 2A-B inflates to a larger diameter than unmodified areas of the body region 108 because it has lower resistance to the air pressure inside the inflatable device. This reduces dog-bone effects at the ends and decreases the likelihood of damage to surrounding tissue. At the same time, the ultrashort laser pulse-formed recession leaves the adjacent surface polymer network morphology substantially unaffected by thermal effects.

Figure 3:
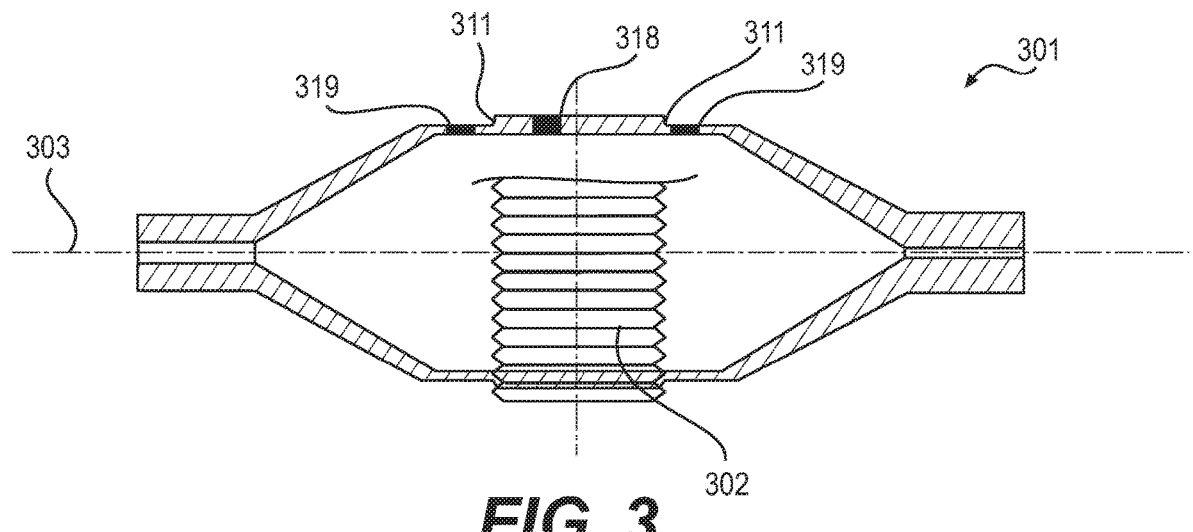
FIG. 3 is a schematic of another inflatable device after modification with low heat laser pulses.

FIG. 3 shows another inflatable device 301 with recessions 311 formed by ultrashort laser pulses. In this implementation, the outer portion of the surface of the body region 308 has been ablated by ultrashort laser pulses so as to create two recessions 311 in the surface of the body region. The recessions 311 have lengths that extend parallel to the longitudinal axis 303. The recessions 311 extend fully around the perimeter forming two cylindrical strips on opposite sides of the valve 302. The wall of the body region has an original thickness 318 and an ablated wall thickness 319. The original thickness 318 corresponds to thickness 118 of the unmodified inflatable device 101 shown in FIG. 1A.

Certain areas of the body region of an unmodified inflatable device (such as the one shown in FIG. 1A) can inflate before others, which can result in slight axial movements of the valve or stent. The ultrashort laser pulse-formed recessions 311 of FIG. 3 have lower resistance to the air pressure inside the inflatable device. They inflate to a wider diameter than the unmodified areas of the body region. They also inflate prior to the region that is under the valve or stent 302. These aspects reduce axial movements of the valve or stent 302 during inflation.

Figure 4A:
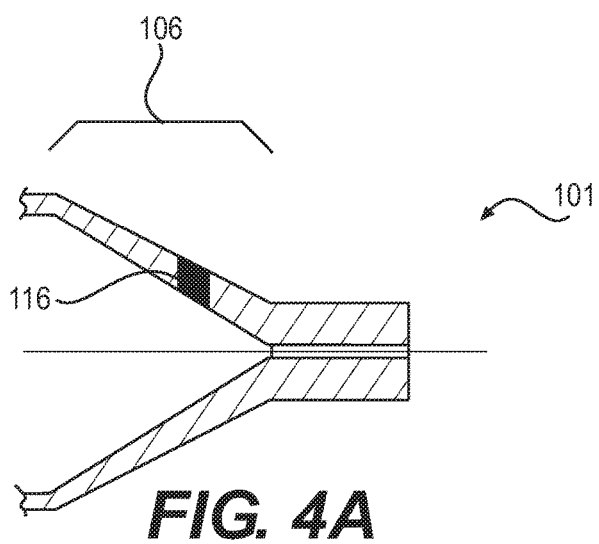
FIG. 4A depicts the cone region of an inflatable device prior to modification with low heat laser pulses.
Figure 4B:
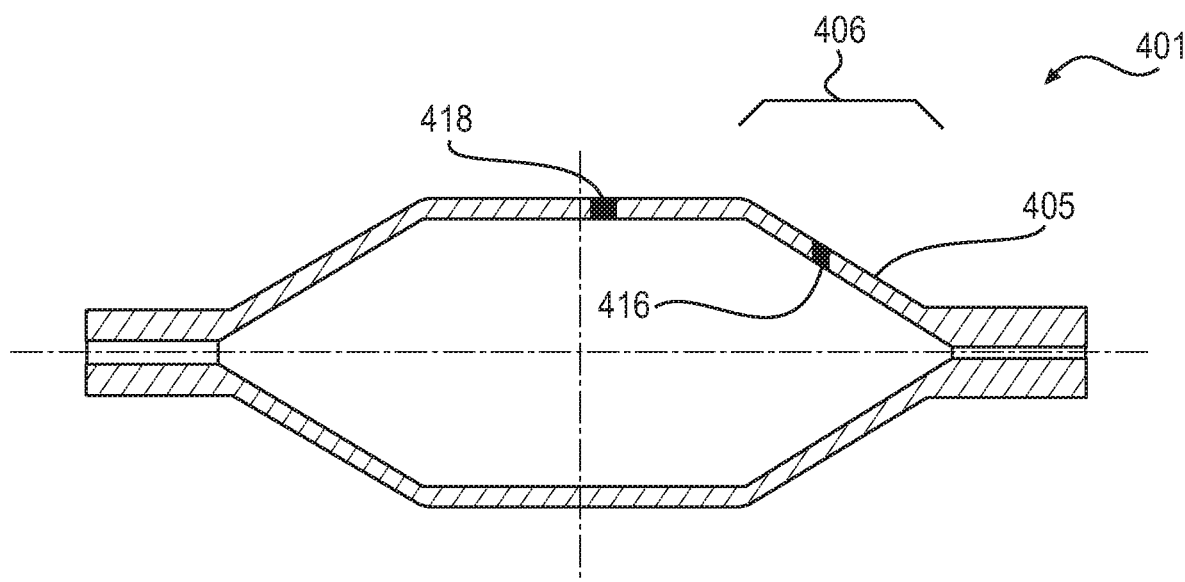
FIG. 4B depicts an inflatable device with low heat laser pulse formed modifications in the cone region.

FIG. 4A shows an enlarged view of the cone 106 and leg regions 104 of the inflatable device 101 shown in FIG. 1A. FIG. 4B shows the inflatable device 401 after ultrashort laser pulse formed modifications to the outer surface 405 of the cone region 406. In this implementation, excess material is ablated fully cylindrically around the perimeter of the outer surface 405 of the cone region 406. Advantageously, the reduced cone thickness 416 facilitates tighter folding of the inflatable device. This enables the device to be used in narrower anatomical spaces.

Figure 5A:
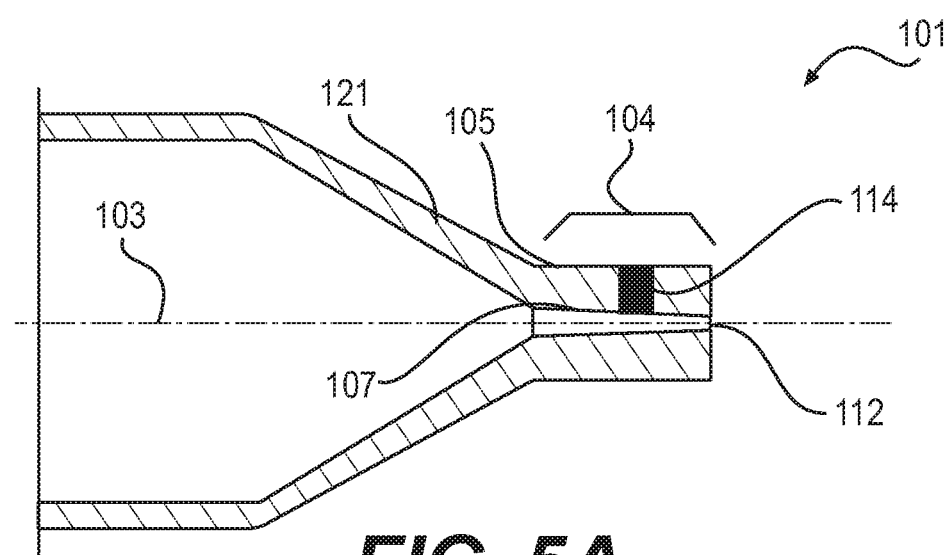
FIG. 5A depicts the leg region of an inflatable device prior to modification with low heat laser pulses.

FIG. 5A shows an enlarged view of the unmodified inflatable device shown in FIG. 1A. Notably, the inner surface 107 of the leg region 104 has a tapered shape defining the axial opening 112.

Figure 5B:
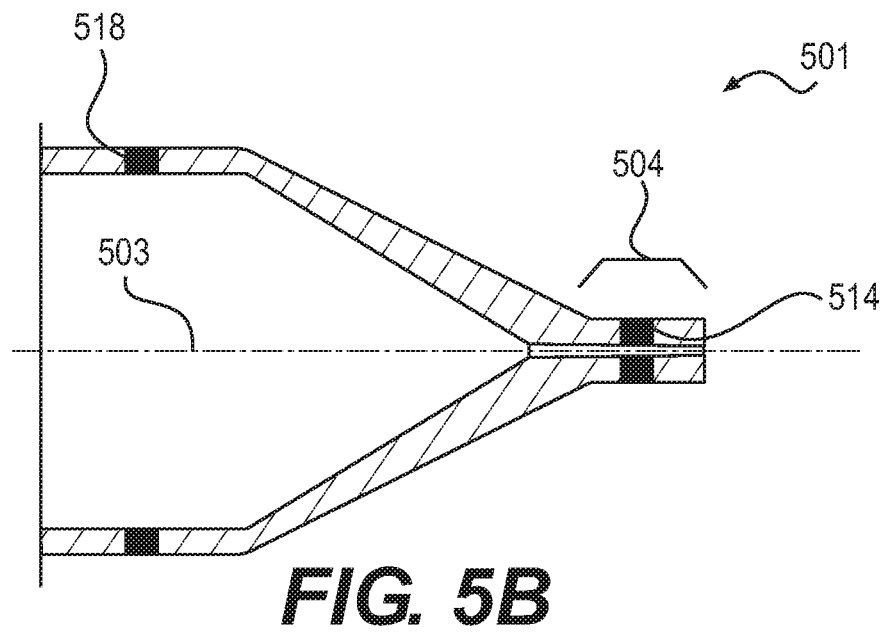
FIGS. 5B-D show inflatable devices with low heat laser pulse formed modifications to the leg region.
Figure 5C:
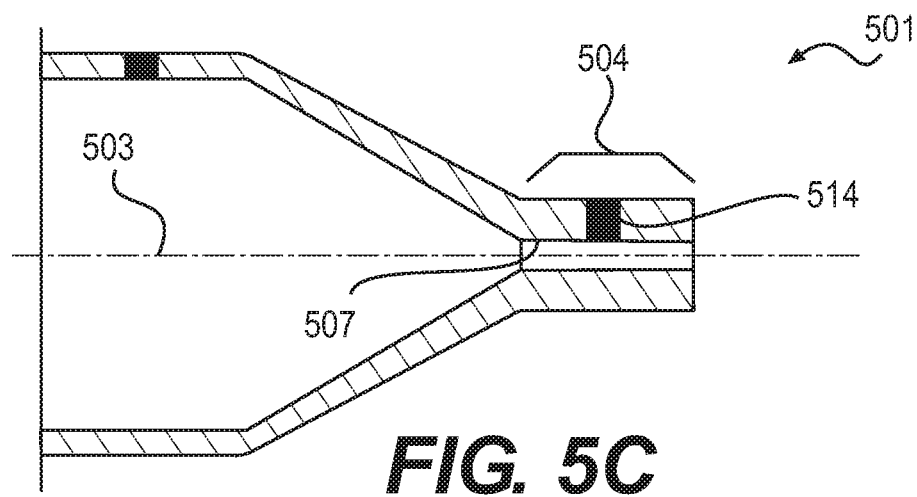
Figure 5D:
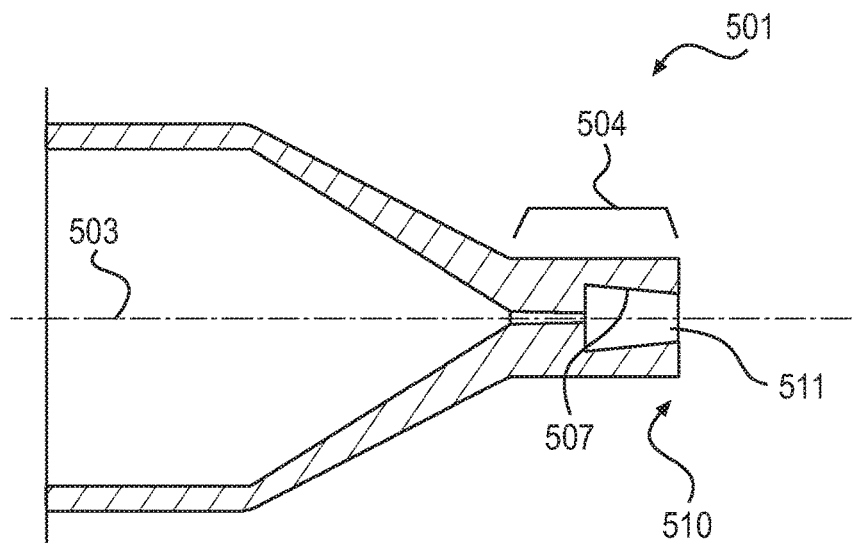

FIGS. 5B-D show inflatable devices 501 after ultrashort laser pulse formed modifications to the leg region 104. In particular, FIG. 5B shows the original outer surface 105 of the leg region 104 ablated, creating the diminished leg region wall thickness 514. The ablation of the excess material extends circumferentially around the perimeter of the leg region 504. The reduction in leg thickness enables tighter folding of the inflatable device.

As described above and as demonstrated in FIG. 5A, the necking process can lead to unevenness in the wall 121 along the length of the leg region. In the implementation shown in FIG. 5C, low-heat laser pulses have been directed through the outer surface of the leg region to ablate the original inner surface 107 of the leg region 104. This creates a thinned inner surface 507 and diminished leg region wall thickness 514. This allows for a larger wire or other mating part to fit within the opening 507 for better bonding. In addition to enabling tighter folding, the ablation creates a smoother inner surface 507 to raise bonding strength to external devices such as catheters and guidewires. In addition, less and/or more consistent thickness leg material will generate a more consistent heating profile (and better bonding) during, for example, a heat-fusion bonding process. Laser etching of the leg material can occur before or after bonding. After etching the inner surfaces of an inflatable device, the device can undergo a cleaning process, such as ultrasonic cleaning, to remove debris prior to use in a patient.

FIG. 5D shows another inflatable device 501 with a bonding feature 511 in the leg region 504. The bonding feature 511 is created by ablation of part of the inner surface 507 by ultrashort laser pulses. The bonding feature 511 extends from the end 510 of the leg region along the longitudinal axis 503. The shape of the bonding feature 511 can be frustoconical, wedge, tapered or hook shaped, for example, or can be some increase in surface roughness. The bonding feature 511 reduces longitudinal slippage of an external device, such as a catheter or guidewire, that has been bonded to inner surface 507 of the inflatable device. For example, the wedge shape of bonding feature 511 in FIG. 5D can mate with a flare at an end of a catheter or guidewire, raising the force necessary to decouple the catheter or guidewire from the inflatable device.

Figure 6:
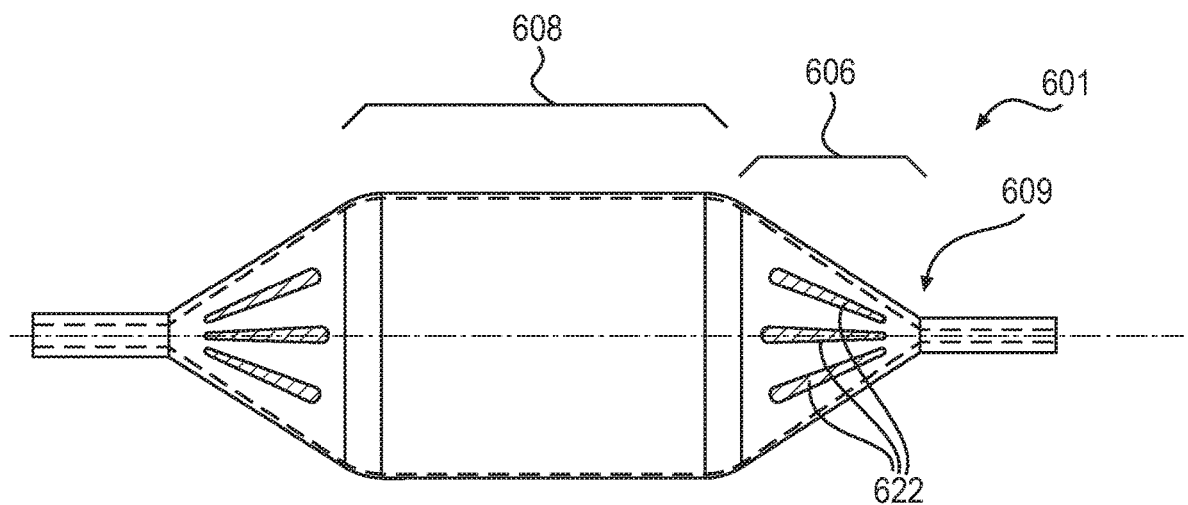
FIG. 6 is a schematic of an inflatable device with low heat laser pulse formed modifications to the cone regions.

FIG. 6 shows an inflatable device 601 with ultrashort laser pulse-formed recessions 622 in the inflatable device 101 of FIG. 1A. In this implementation, the recessions 622 are formed on the cone region 606. The recessions 622 can extend from adjacent the end 609 of the cone region 606 in the direction of the body region 608. The width of recessions 622 can taper gradually from larger proximate the body region 608 toward the end of the cone region 609. Recessions 622 promote folding in specified locations, leading to better organization of the folds and thus tighter folding.

Figure 7A:
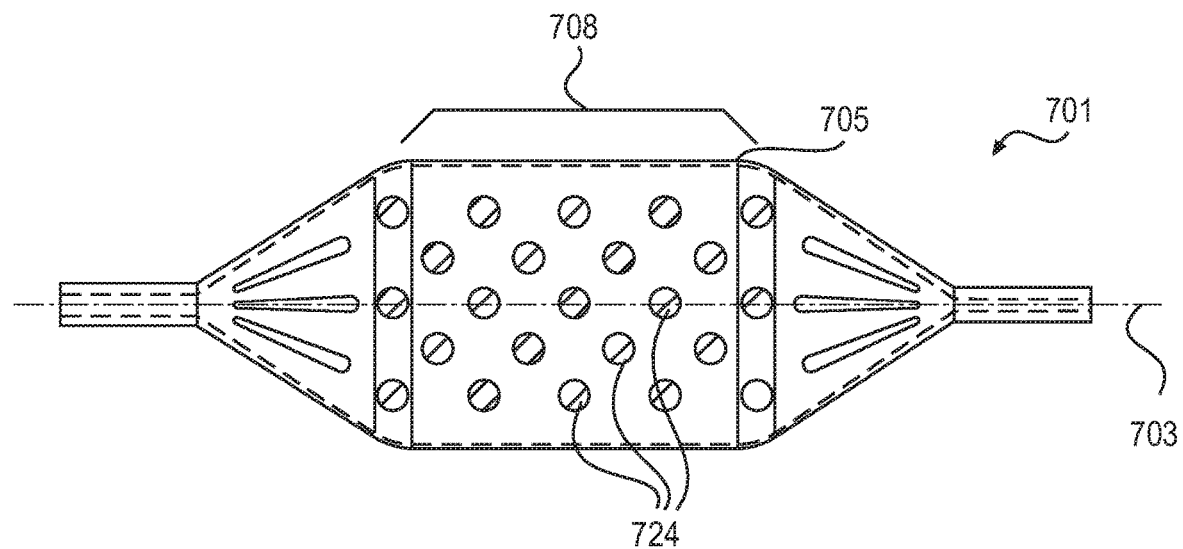
FIGS. 7A-C are schematics of inflatable devices with low heat laser pulse formed modifications to the body regions.
Figure 7B:
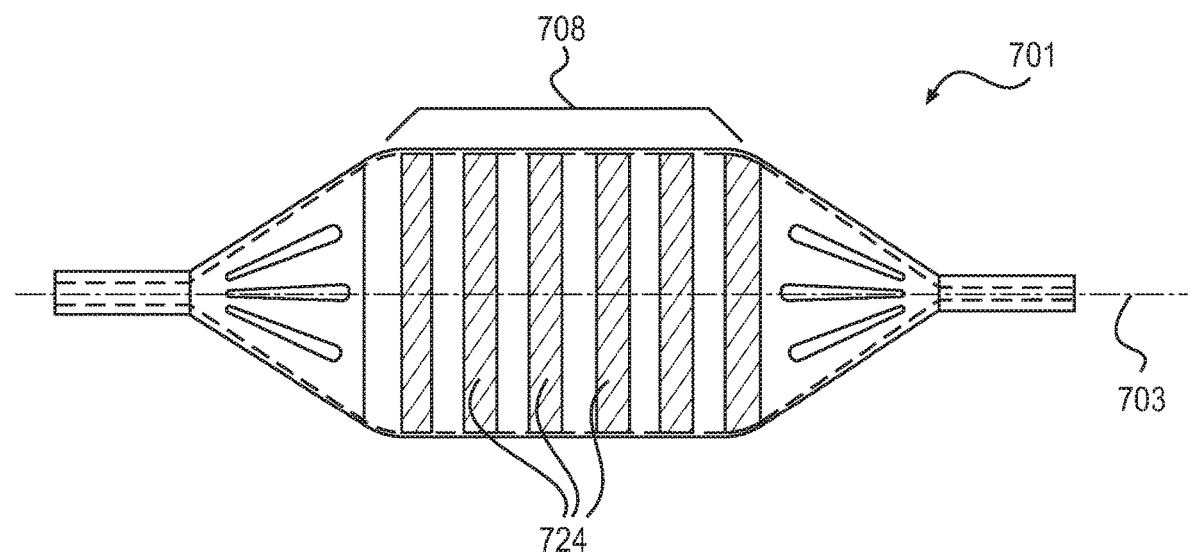
Figure 7C:
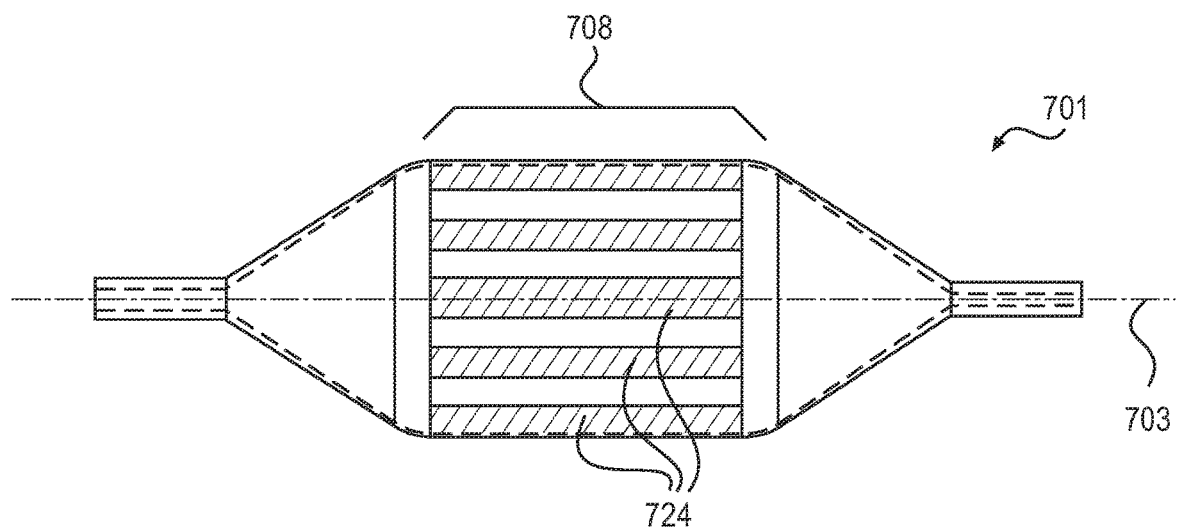

FIGS. 7A-C show implementations for increasing the frictional force between the inflatable device 701 and an above-lying surface. Recessions 724 are ablated onto the body region 708 using ultrashort laser pulses. The increased frictional force induced by these recessions decreases movement of a valve or stent along the body region of the inflatable device, improving the consistency and safety of the procedure.

FIG. 7A shows an inflatable device 701 with circular ultrashort laser pulse-formed recessions 724 for increased frictional force. A plurality of recessions 724 can be uniformly or randomly spaced around the outer surface 705 of the body region 708. While the recessions of this implementation are shown as circles, recessions 724 can be other shapes such as squares, rectangles, or triangles. These recessions prevent both axial and circumferential slippage of the valve or stent. Different patterns of different types of recessions can be employed on different parts of the inflatable device, such as circles of one diameter on the body region and circles of another diameter on the cone regions.

The implementation shown in FIG. 7B has a plurality of ultrashort laser pulse-formed recessions 724 that extend circumferentially around the perimeter of the device. The recessions have a width in the direction parallel to the longitudinal axis 703 and a depth into the outer portion 705 of the surface of the body region. The recessions 724 are spaced along the longitudinal axis 703. The circumferential orientation of the recessions 724 helps to prevent slippage of the stent or other device in the direction of the longitudinal axis 703.

The implementation shown in FIG. 7C has a plurality of ultrashort laser pulse-formed recessions 724 that extend across the body region 708 in the direction of the longitudinal axis 703. The recessions are spaced around the circumference of the body region 708. The longitudinal orientation of the recessions helps to prevent slippage of the stent or other device around the circumference of the body region 708.

Figure 8A:
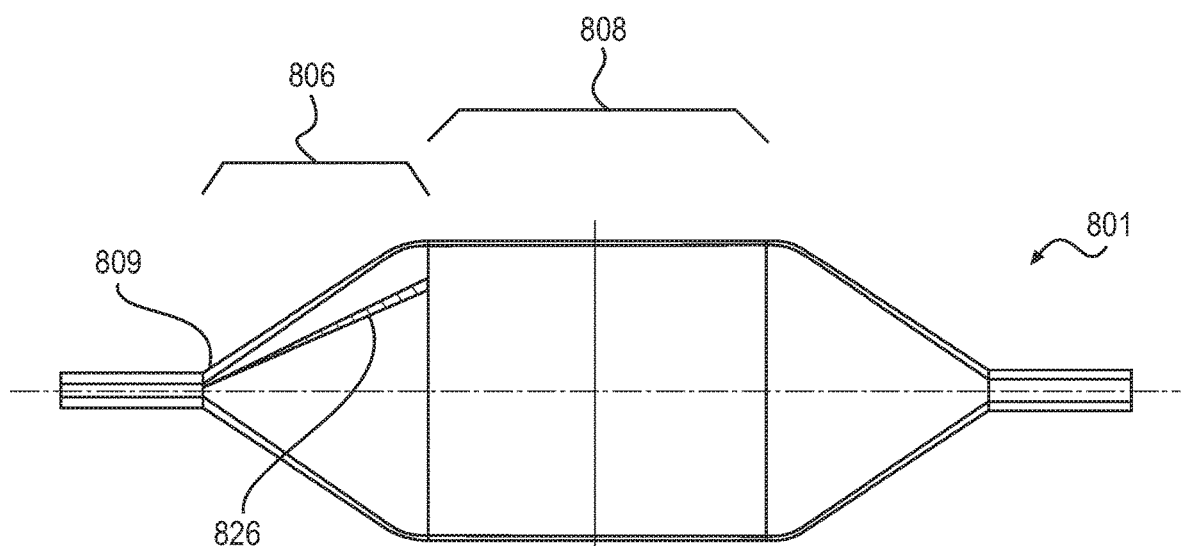
FIGS. 8A-C are schematics of inflatable devices with low heat laser pulse formed modifications along the longitudinal axis.
Figure 8B:
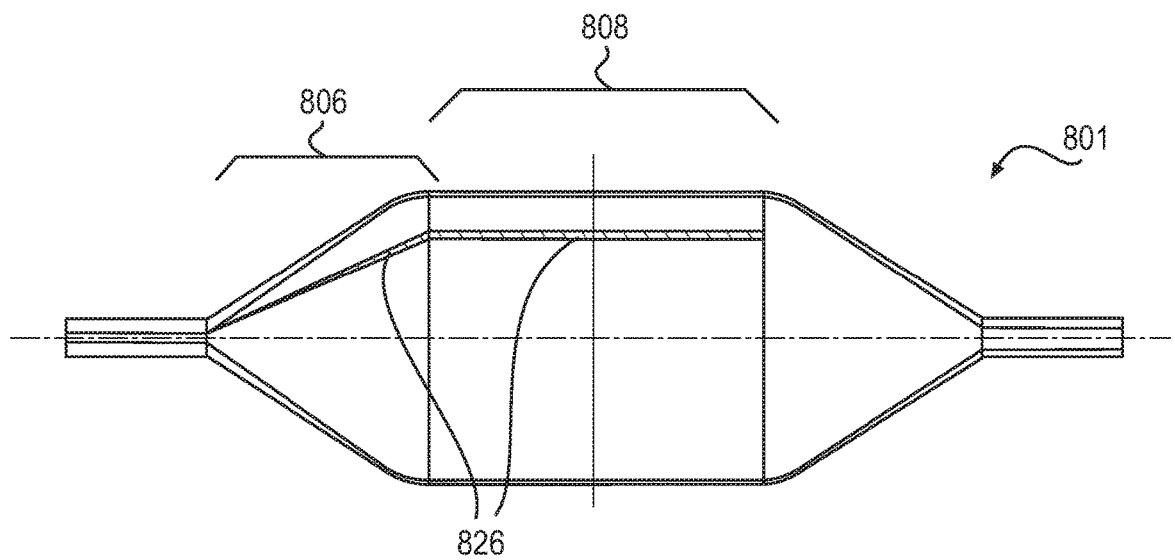
Figure 8C:
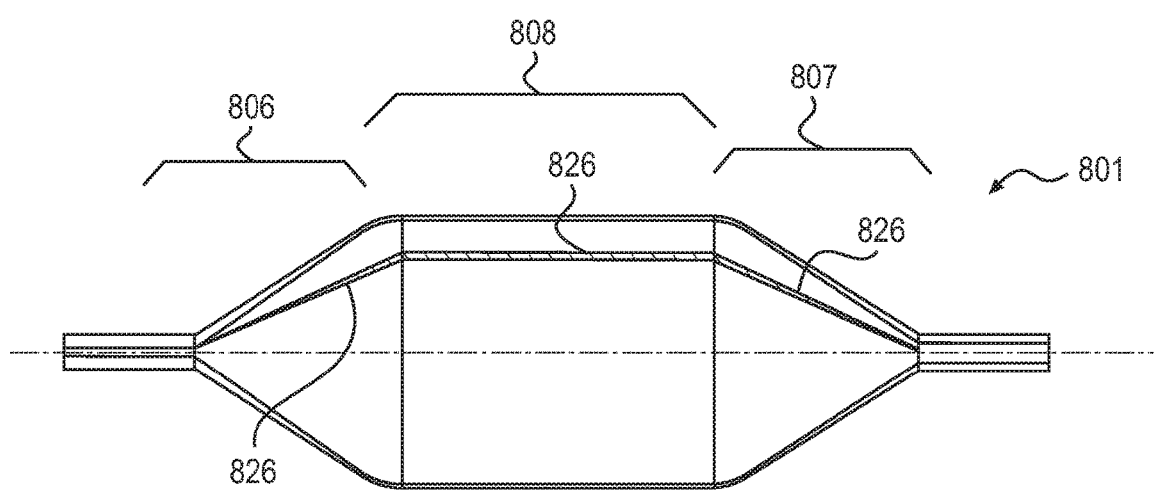

FIGS. 8A-C show inflatable devices 801 designed to burst at specific locations if inflated past predetermined pressures. In particular, the ultrashort laser pulse-formed modifications are tailored to weaken the wall in a particular pattern. This results in a predictable burst pattern when the inflatable device is overinflated, which can make it easier to retrieve a ruptured device. The recessions can also promote slow, gentle leaking of air (or other fluids) in the event of overinflation, as opposed to bursting.

In the implementation of FIG. 8A, an ultrashort laser pulse-formed recession 826 extends from adjacent end 809 of the cone region 806 in the direction of the body region 808. In the implementation of FIG. 8B, the ultrashort laser pulse-formed recession 826 extends from adjacent the end 809 of the cone region 806 and across the body region 808. In the implementation of FIG. 8C, the recession 826 extends from adjacent the end 809 of the cone region 806, across the body region 808, and toward the end of the second cone region 807.

In FIGS. 8A-C, the bursting pattern would occur in the longitudinal direction. This facilitates retrieval of a ruptured inflatable device. Or, the longitudinal etched recessions will result in a gentler leakage as opposed to bursting. Another advantage is that the axial recessions 826 can promote axial blood perfusion, enabling blood or drug flow around the inflatable device during and after inflation.

Figure 9:
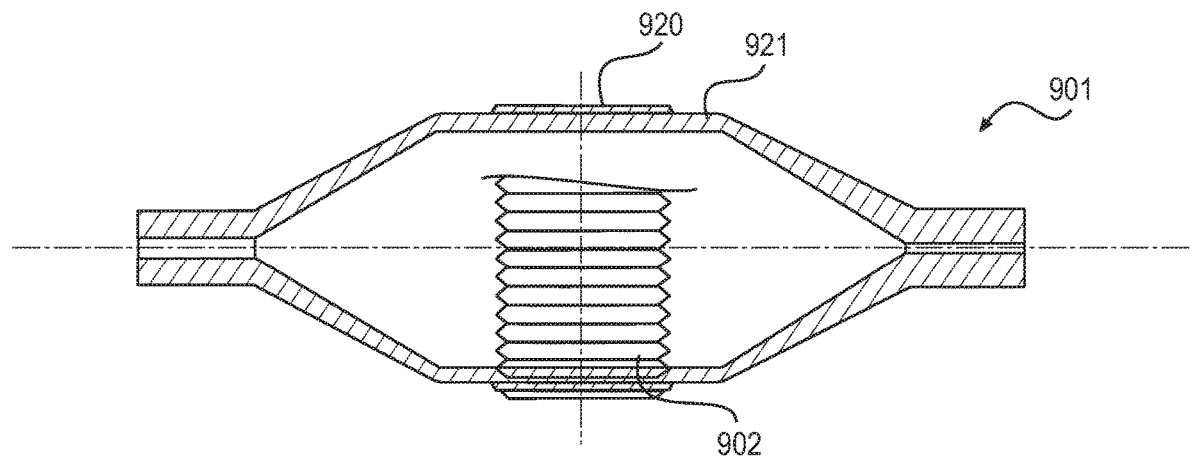
FIG. 9 is a schematic of an inflatable device.

FIG. 9 shows an inflatable device 901 with modifications of a multi-layer inflatable device, such as the device 101 of FIG. 1C. Parts of the outer layer 920 have been removed by ultrashort laser pulses, exposing the inner layer 921. The remaining outer layer 920 extends as a circumferential, tubular shaped layer around the perimeter of the inflatable device 901. The length of outer layer 920, as measured parallel to the longitudinal axis 903, can be formed to substantially match the length of an external device, such as a stent mounted heart valve 902. The outer layer 920 of FIG. 9 can have different properties than the inner layer 921. For example, the outer layer 920 can change the frictional properties between the inflatable device 901 and an above-lying surface. Meanwhile, ablation of the excess outer surface material allows for tighter folding of the inflatable device 901.

Figure 10:
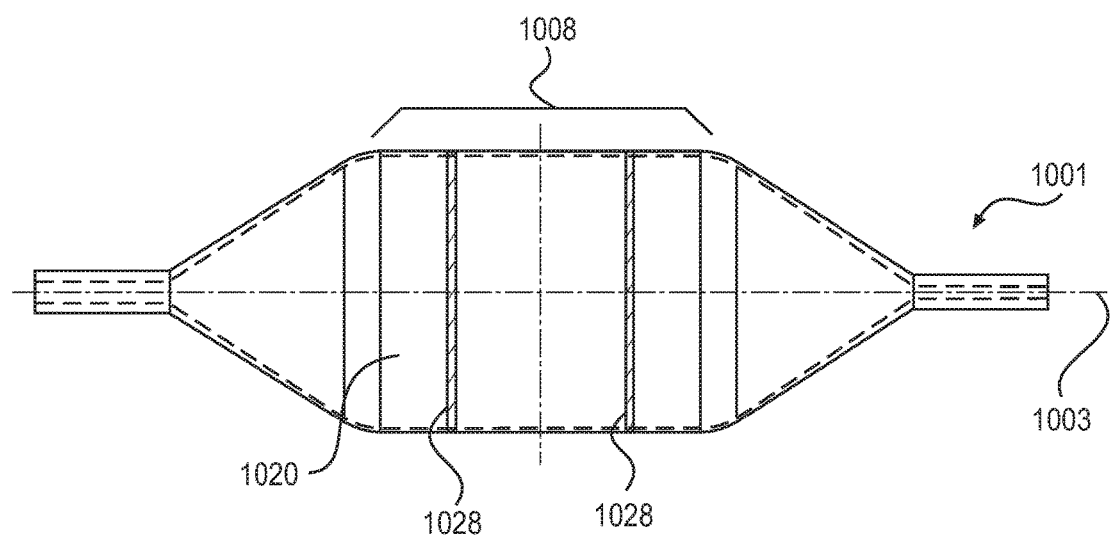
FIG. 10 is a schematic of an inflatable device.

FIG. 10 shows an inflatable device 1001 with recessions 1028 formed by ultrashort laser pulses to serve as identifying marks. Recessions 1028 can be located on the body region 1008 as seen in FIG. 10. The recessions 1028 can also (additionally or alternatively) be located on the cone region or the leg region. In FIG. 10, recessions 1028 extend circumferentially around the perimeter of the body region 1008. These recessions can serve as identifying marks to assist in the assembly of the inflatable device. Markings on the inflatable device leg can help identify cutting length or welding bands, for example. They can also assist in the alignment of the stent or valve during anatomical implantation. Markings can have indicia to identify parts, product models and inflatable device sizes as another example.

The implementation of FIG. 10 can also have multiple layers—such as a radiopaque outer layer 1020. The recessions 1028 in the outer layer selectively remove the radiopaque outer layer 1020, for example, to reveal its orientation on radiological instruments during medical procedures.

The ultrashort laser pulse formed modifications disclosed herein have the advantage of having low or no thermal impact on the inflatable device wall. The absence of significant thermal impact preserves the properties of the inflatable device. For example, use of the ultrashort laser preserves the homogeneity of the polymer orientation of a polymeric wall.

Advantageously, the inflatable devices disclosed herein can be used to improve various inflatable device based medical procedures, such as to deliver a prosthetic heart valve during a transcatheter valve replacement procedure. As another example, the devices can be used to deliver a stent during percutaneous procedures. As another advantage, the laser etching procedure disclosed herein allows the thickness of the cone and body of a device to be changed independently—facilitating variations in expansion characteristics. Also, uniform wall thickness facilitates folding, retrieving and better general performance. For example, the legs of the inflatable device need to be thicker to allow stretching of the body without breaking the inflatable device. Laser etching allows the legs to be thinned for a lower profile, reducing friction on the arterial walls during deployment and retrieval.

The various patterns of recession etching disclosed herein have a range of advantages. Reduction in body wall thickness results in resistance to formation of the dumb-bell (or dog bone) shape during expansion of a stent or valve, resulting in a more accurate final outside diameter for the device being delivered. This can be useful for aortic applications. Ablating one end selectively can result in a mushroom shape, which can be helpful for bicuspid repair. Reduction of the cone region thickness reduces inflatable device withdrawal forces. Ablating shallow rings in the body at one or both ends facilitates earlier expansion of ring portions to limit axial movement of the stent or valve. Ablating shaped patterns in the outer surface of the inflatable device wall increase the friction force between the implantable and the inflatable device. Removal of wall material in an axial direction (or other location) can create a desired point, spot or pattern for failure of the inflatable device. Reduction of leg thickness reduces bond profiles and increases efficiency of the bonding process. Also, shaping of the leg regions can increase bond strength and precision.

Also, in multi-layered inflatable devices, the low-heat laser can be used to remove undesired layers from various locations. A dual layer can be retained in the body region for increased puncture resistance and increased (or decreased) friction between the inflatable device and stent, but removed from the cone and leg regions for profile and tackiness reduction. The inflatable device can also be modified to create "witness lines" or a mid-line to improve alignment of the inflatable device and stent or valve during crimping or other assembly steps. Or, the inflatable device can be etched with various identification marks.

Removal of wall materials from a center or body section reduces stent or valve frame edge flaring, reducing impact on surrounding tissues during delivery. A tapered wall inflatable device could also be created to create a tapered outer or inner diameter in the vasculature, stent or valve frame, to fit tapered anatomy, such as in the peripheral vasculature, for example.

Many modifications and other embodiments of the invention set forth herein will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method of fabricating a transcatheter device having an inflatable balloon, the method comprising:
   obtaining a polymer tube defining a longitudinal axis, the polymer comprising a network of polymer chains with a homogenous network morphology;
   blow molding the polymer tube into a hollow balloon shape having a wall defined by wall regions including a central body region, a pair of leg regions on opposite ends of the balloon shape that are radially smaller than the central body region and define axial openings therethrough, and a pair of cone regions extending between the body region and the leg regions, the wall in each wall region having an outer surface and an inner surface; and
   applying low heat laser pulses to portions of either the outer surface or inner surface of at least one wall region to form a laser-formed modification, the low heat laser pulses being configured so as to leave the polymer network morphology surrounding the laser-formed modification substantially unchanged, wherein the low heat laser pulses are applied to the central body region to form a recession that extends parallel to the longitudinal axis and around a circumferential perimeter of the central body region to reduce the wall thickness in a portion thereof.

2. The method of claim 1, wherein the low heat laser pulses are less than 1000 picoseconds in duration.

3. The method of claim 1, wherein the low heat laser pulses are applied to an outer surface of the cone regions to create a constant wall thickness in the cone regions.

4. The method of claim 1, wherein the low heat laser pulses are applied to an outer surface of the cone regions to create a plurality of longitudinal recessions in the cone regions.

5. The method of claim 1, wherein the step of applying is done prior to the step of blow molding.

6. The method of claim 1, wherein the low heat laser pulses are applied to the leg regions and create a diminished wall thickness of the leg region.

7. The method of claim 1, wherein the low heat laser pulses are applied to the leg regions and create a wedge, a taper, or an increase in surface roughness on the inner surface of the leg regions.

8. The method of claim 1, wherein the central body region has an original thickness and an ablated wall thickness, and the ablated wall thickness is between about 1-40% of the original wall thickness.

9. The method of claim 1, further including folding the balloon and crimping a heart valve around the reduced wall thickness portion of the central body region.

10. A method of fabricating a transcatheter device having an inflatable balloon, the method comprising:

obtaining a polymer tube defining a longitudinal axis, the tube having at least two polymer wall layers including an outer layer farthest from the longitudinal axis and an inner layer, the polymers in each respective outer or inner layer comprising a network of polymer chains with a homogenous network morphology;

blow molding the polymer tube into a hollow balloon shape having a wall defined by wall regions including a central body region, a pair of leg regions on opposite ends of the balloon shape that are radially smaller than the central body region and define axial openings therethrough, and a pair of cone regions extending between the body region and the leg regions, the wall in each wall region having an outer surface formed by the outer layer and an inner surface formed by the inner layer; and applying low heat laser pulses to portions of either the outer surface or inner surface of at least one wall region to form a laser-formed modification, the low heat laser pulses being configured so as to leave the polymer network morphology surrounding the laser-formed modification substantially unchanged, wherein there are more than two polymer wall layers.

11. The method of claim 10, wherein the outer layer is radiopaque.

12. The method of claim 10, wherein the outer layer is removed in a pattern that indicates an orientation of the balloon on radiological instruments.

13. The method of claim 10, wherein the outer layer is radiopaque.

14. The method of claim 10, wherein the polymer of the outer layer is inherently rougher than the polymer of the inner layer, and the low heat laser pulses are applied to the cone regions to facilitate passage of the balloon through body lumens.

15. The method of claim 10, wherein the low heat laser pulses are applied to the central body region wherein the outer layer is removed to expose the inner layer, wherein a remaining portion of the outer layer extends as a circumferential, tubular shaped layer around the perimeter of the inflatable device.

16. The method of claim 10, further including folding the balloon and crimping a heart valve around the central body region, wherein a length of the remaining portion of the outer layer substantially matches a length of the heart valve.

17. A method of fabricating a transcatheter device having an inflatable balloon, the method comprising:
obtaining a polymer tube defining a longitudinal axis, the polymer comprising a network of polymer chains with a homogenous network morphology;

blow molding the polymer tube into a hollow balloon shape having a wall defined by wall regions including a central body region, a pair of leg regions on opposite ends of the balloon shape that are radially smaller than the central body region and define axial openings therethrough, and a pair of cone regions extending between the body region and the leg regions, the wall in each wall region having an outer surface and an inner surface; and applying low heat laser pulses to portions of either the outer surface or inner surface of at least one wall region to form a laser-formed modification, the low heat laser pulses being configured so as to leave the polymer network morphology surrounding the laser-formed modification substantially unchanged, wherein the low heat laser pulses are applied to the central body region and form recessions that enhance a frictional capacity of the central body region.

18. The method of claim 17, further including folding the balloon and crimping a heart valve around the central body region.

19. A method of fabricating a transcatheter device having an inflatable balloon, the method comprising:
obtaining a polymer tube defining a longitudinal axis, the tube having at least two polymer wall layers including an outer layer farthest from the longitudinal axis and an inner layer, the polymers in each respective outer or inner layer comprising a network of polymer chains with a homogenous network morphology;

blow molding the polymer tube into a hollow balloon shape having a wall defined by wall regions including a central body region, a pair of leg regions on opposite ends of the balloon shape that are radially smaller than the central body region and define axial openings therethrough, and a pair of cone regions extending between the body region and the leg regions, the wall in each wall region having an outer surface formed by the outer layer and an inner surface formed by the inner layer; and applying low heat laser pulses to portions of either the outer surface or inner surface of at least one wall region to form a laser-formed modification, the low heat laser pulses being configured so as to leave the polymer network morphology surrounding the laser-formed modification substantially unchanged, wherein the low heat laser pulses are applied to the central body region wherein the outer layer is removed to expose the inner layer, wherein a remaining portion of the outer layer extends as a circumferential, tubular shaped layer around the perimeter of the inflatable device.

20. A method of fabricating a transcatheter device having an inflatable balloon, the method comprising:
obtaining a polymer tube defining a longitudinal axis, the tube having at least two polymer wall layers including an outer layer farthest from the longitudinal axis and an inner layer, the polymers in each respective outer or inner layer comprising a network of polymer chains with a homogenous network morphology;

blow molding the polymer tube into a hollow balloon shape having a wall defined by wall regions including a central body region, a pair of leg regions on opposite ends of the balloon shape that are radially smaller than the central body region and define axial openings therethrough, and a pair of cone regions extending between the body region and the leg regions, the wall in each wall region having an outer surface formed by the outer layer and an inner surface formed by the inner layer; and applying low heat laser pulses to portions of either the outer surface or inner surface of at least one wall region to form a laser-formed modification, the low heat laser pulses being configured so as to leave the polymer network morphology surrounding the laser-formed modification substantially unchanged, further including folding the balloon and crimping a heart valve around the central body region, wherein a length of the remaining portion of the outer layer substantially matches a length the heart valve.

* * * * *